US007053029B2

(12) United States Patent
MacDonald et al.

(10) Patent No.: US 7,053,029 B2
(45) Date of Patent: May 30, 2006

(54) USE INDICATING SOAP

(75) Inventors: John Gavin MacDonald, Decatur, GA (US); Naveen Agarwal, Atlanta, GA (US); Yanbin Huang, Roswell, GA (US); Jaeho Kim, Roswell, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 289 days.

(21) Appl. No.: 10/107,383

(22) Filed: Mar. 27, 2002

(65) Prior Publication Data

US 2003/0191036 A1 Oct. 9, 2003

(51) Int. Cl.
*A61K 7/00* (2006.01)

(52) U.S. Cl. .............. 510/130; 510/158; 510/169; 510/481; 510/488; 510/491; 510/508

(58) Field of Classification Search .................. None
See application file for complete search history.

(56) References Cited

U.S. PATENT DOCUMENTS

| | | | |
|---|---|---|---|
| 3,669,891 A | 6/1972 | Greenwood et al. | |
| 4,013,475 A | 3/1977 | Liebowitz et al. | |
| 4,082,682 A | 4/1978 | Inamorato et al. | |
| 4,102,995 A | 7/1978 | Hebborn | |
| 4,111,853 A | 9/1978 | Shultz et al. | |
| 4,335,103 A | 6/1982 | Barker et al. | |
| 4,532,132 A | 7/1985 | Keil | |
| 4,704,224 A | 11/1987 | Saud | |
| 4,954,544 A | 9/1990 | Chandaria | |
| 4,999,348 A | 3/1991 | Cioca et al. | |
| 5,021,183 A | 6/1991 | Saud | |
| 5,064,635 A | 11/1991 | Casey | |
| 5,215,757 A | 6/1993 | El-Nokaly | |
| 5,246,614 A | 9/1993 | Baumgartner et al. | |
| 5,266,321 A | 11/1993 | Shukuzaki et al. | |
| 5,304,334 A | 4/1994 | Lahanas et al. | |
| 5,427,708 A | 6/1995 | Stark | |
| 5,447,962 A | 9/1995 | Ajioka et al. | |
| 5,486,228 A | 1/1996 | Miller et al. | |
| 5,502,158 A | 3/1996 | Sinclair et al. | |
| 5,569,692 A | 10/1996 | Bastioli et al. | |
| 5,597,556 A | 1/1997 | Moghe et al. | |
| 5,599,555 A | 2/1997 | El-Nokaly | |
| 5,606,016 A | 2/1997 | Maeda et al. | |
| 5,614,564 A | 3/1997 | Hwang et al. | |
| 5,626,853 A | 5/1997 | Bara et al. | |
| 5,645,822 A | 7/1997 | Meyer et al. | |
| 5,688,831 A | 11/1997 | El-Nokaly et al. | |
| 5,714,230 A | 2/1998 | Kameoka et al. | |
| 5,756,438 A | 5/1998 | Rau et al. | |
| 5,763,098 A | 6/1998 | Kameoka et al. | |
| 5,852,114 A | 12/1998 | Loomis et al. | |
| 5,876,995 A | 3/1999 | Bryan | |
| 5,891,428 A | 4/1999 | Greff | |
| 5,906,783 A | 5/1999 | Narayan et al. | |
| 6,113,886 A | 9/2000 | Bryan | |
| 6,120,803 A | 9/2000 | Wong et al. | |
| 6,152,358 A | 11/2000 | Bryan | |
| 6,174,535 B1 | 1/2001 | Lundmark | |
| 6,184,261 B1 | 2/2001 | Biby et al. | |
| 6,194,517 B1 | 2/2001 | Pomplun et al. | |
| 6,224,852 B1 | 5/2001 | Morgan et al. | |
| 6,228,822 B1 | 5/2001 | Allison et al. | |
| 6,247,995 B1 | 6/2001 | Bryan | |
| 6,395,701 B1 * | 5/2002 | Connor et al. .............. 510/437 |
| 6,428,799 B1 * | 8/2002 | Cen et al. .................... 424/402 |
| 6,491,933 B1 * | 12/2002 | Lorenzi et al. ............. 424/401 |
| 6,565,865 B1 * | 5/2003 | Bekele ........................ 424/401 |
| 6,713,075 B1 * | 3/2004 | Bekele ........................ 424/401 |

FOREIGN PATENT DOCUMENTS

| | | |
|---|---|---|
| EP | 0 266 124 | 5/1988 |
| EP | 0 284 765 | 10/1988 |
| EP | 0418049 | 3/1991 |
| EP | 0 850 039 | 7/1998 |
| FR | 2717184 | 9/1995 |
| FR | 2805162 | 8/2001 |
| GB | 2348646 A | 11/2000 |
| WO | 96/32925 | 4/1995 |
| WO | WO 96/29047 | 9/1996 |
| WO | WO 01/19946 A1 | 3/2001 |

OTHER PUBLICATIONS

Derwent Abstract, FR 2805162, Aug. 24, 2001, Casella J C.
CDC (Rev. by Julia S. Garner, R.N., M.N. and Martin S. Favero, Ph.D.); *Guideline for Handwashing and Hospital Environmental Control*, 1985; 1-27.
E. L. Larson and 1992, 1993, and 1994 APIC Guidelines Committee Assn. for Professionals in Infection Control and Epidemiology, Inc.; *APIC Guideline for Hand Washing and Hand Antiepsis in Health-Care Settings\**; 1995; 1-17.
US 6,290,977, 09/2001, Friars et al. (withdrawn)

\* cited by examiner

*Primary Examiner*—Necholus Ogden
(74) *Attorney, Agent, or Firm*—Dority & Manning

(57) ABSTRACT

There is provided a soap that contains an indicator that produces an observable change after a period of time to show that sufficient cleaning has been done or to indicate the thoroughness of the cleaning. The soap is preferably made from two components that produce a color and/or viscosity changes after about 30 seconds of use. This use indicating change is useful for, for example, teaching children to was their hands for a sufficient period of time.

14 Claims, No Drawings

USE INDICATING SOAP

BACKGROUND OF THE INVENTION

The present invention concerns soap for hand, body and surface washing.

Soap and water are effective cleaners and, depending on ingredients, can be effective in fighting bacteria and other causes of illness. In many cases, effective cleaning and disease control occur only after certain periods of time or at elevated temperatures. While it may be a relatively simple matter for adults to judge the appropriate time for washing, this is not always the case with children. Children, whether in brushing teeth or washing hands, for example, tend to spend less time on the task than desired by parents and other caregivers. This can result in ineffective cleaning.

It is, therefore, quite important for children to learn the correct way of completing a key hygiene task such as brushing teeth or washing hands. In order for these habits to form at an early age, parents or guardians typically rely on constant reminders and close monitoring. It takes a lot of time and attention from the parent or the guardian in their attempts to build and reinforce these hygiene habits. Further, children tend to follow the instructions only as long as they feel they are being monitored. Most often, children grow up learning these habits only as a result of pressure from their parents or guardians, and do not maintain these habits once the pressure of close monitoring is absent.

An important aspect of building these hygiene habits is to involve the children in completing the task in a way that focuses their attention on the hygiene activity in a non-threatening and natural manner. One way of accomplishing this would be to introduce an element of fun and play so that children enjoy completing the task while building these habits. Another way would be give them a sense of accomplishment by providing a feedback signal they can easily understand and associate with correctly completing the task. If there is an element of fun and play in addition to a clear feedback indication, children are likely to complete the hygiene task without any need for close supervision and monitoring by their parents and guardians.

Various approaches have been used to remedy this problem. In the case of tooth brushing, flavored toothpastes have been developed to encourage children to brush longer, because they like the taste. This approach is not available for soap, however. A clock or timer can also be used but has drawbacks as well.

There remains a need, therefore, for a soap product that may be used by a consumer and which will give an indication of when sufficient use has occurred. It is an object of this invention to provide such a use indicating soap.

SUMMARY OF THE INVENTION

In response to the discussed difficulties and problems encountered in the prior art, a new cleaning aid has been developed wherein the aid contains an indicator that provides a change detectible by a user after a period of time after dispensing has passed. The cleaning aid may be, for example, a soap, and the change may be in color, in viscosity, in smell, temperature or even in sound. The observable change may occur in from a finite time to at most 5 minutes or more particularly about 45 seconds, or still more particularly between 15 and 35 seconds.

If the cleaning aid is a soap, the soap is preferably made from a first component including liquid soap and a dye, and a second component including ascorbic acid and iron chloride. The components are mixed together to produce the soap. The soap may change color from green to blue.

The soap may alternatively have liquid soap and polyvinyl alcohol, and optionally, a second component including borax and citric acid. Alternatively, the soap may be liquid soap and a second component, which is an ion sensitive polymeric material. In yet another alternative, the first component may be liquid soap and a polyoxyalkylene block co-polymer, and the second component may include polyacrylic acid. In yet another alternative, the soap may have a first component including liquid soap and a cationic cellulosic quartenary ammonium derivative, and a second component including polyacrylic acid. The components are mixed together to produce the soap.

The soap changes viscosity from a gel to a liquid. The soap changes viscosity in from a finite time to at most 45 seconds after the components are mixed together. More particularly, the soap changes viscosity between 15 and 35 seconds after the components are mixed together.

The soap may alternatively have a first component including liquid soap, a dye and polyvinyl alcohol, and a second component including borax, citric acid, ascorbic acid and iron chloride. The components are mixed together to produce the soap. The soap changes viscosity from a gel to a liquid and simultaneously changes color from green to blue. The soap changes viscosity and color in from a finite time to at most 45 seconds after the components are mixed together. More particularly, the soap changes viscosity and color between 15 and 35 seconds after the components are mixed together.

This invention also encompasses a hygiene teaching aid and a method of developing a hygiene habit. The hygiene teaching aid has an indicator that provides a change detectible to a user after a period of time after dispensing has passed. The method of developing a hygiene habit includes the steps of dispensing soap and water into a user's hands, rubbing the hands together until a change detectible to the user is detected, and washing the hands with water, where the soap contains an indicator that provides the change after a period of time after dispensing the soap into the hands has passed.

DETAILED DESCRIPTION OF THE INVENTION

It has long been a concern to parents that their children wash for a sufficiently long period of time to remove dirt and/or kill any illness causing organisms on their skin. Since children tend to hurry through this task, however, parents are often frustrated in their success in this area. The inventors believe that a soap that indicates when a presumably sufficient time of washing has passed will aid parents and other caregivers in the task of teaching children proper washing techniques. The inventors believe that children will find their soap to be fun and playful and will enjoy using it, thus building and reinforcing proper hygiene habits.

Another aspect of cleaning, more problematic with surface cleaning than in handwashing, is to avoid missing areas entirely. In cleaning a kitchen or bathroom counter, for example, areas may be missed, and there may be no indication that the area has not been washed. An indicator that told the user that all areas he desired to be washed were indeed washed would be important in many areas, such as the cleaning of medical and dental tools, infant bottles and pacifiers, utensils and many more. In this respect, the soap of this invention may be thought of as a cleaning "thoroughness" indicator.

The amount of time needed to clean the skin or a surface has been researched extensively. The Center for Disease Control (CDC), a division of the US Department of Health and Human Service, Public Health Service, has developed guidelines for such cleaning. The CDC *Guideline for Handwashing and Hospital Environmental Control*, 1985 notes at page 7 that "the ideal duration of handwashing is not known, but washing times of 15 seconds or less have been reported as effective in removing most transient contaminants from the skin". The CDC Guidelines at page 9 recommend "for routine handwashing, a vigorous rubbing together of all surfaces of lathered hands for at least 10 seconds, followed by thorough rinsing under a stream of water". The Association for Professionals in Infection Control and Epidemiology (APIC) *Guideline for Hand Washing and Hand Antisepsis in Health-Care Settings* (1995) also recommends a wash time of 10–15 seconds at table 1 for routine hand washing. Antimicrobial soap or detergent or alcohol-based handrub is recommended to remove or destroy transient microorganisms, while soap or detergent are recommended to remove soil and transient microorganisms.

The APIC *Guideline* also notes (page 7) that traditional surgical hand scrubbing is performed in the United States and Europe for 5 minutes. The instant invention may be formulated in such a way as to indicate when larger periods of time have passed by the appropriate choice of ingredients.

In its broadest embodiment, the invention includes soap and an indicator that provides an observable change after a period of time. It preferably contains at least one dye or pre-dye and a modifying agent that causes a change to occur. These components may be kept separate until washing is begun, or may be mixed in a manner such that the change does not occur until washing. Thus the components may be kept in a two part dispenser or may be kept together with one component inactive by some means, such as by microencapsulation, until sufficient physical stimulus results in their effective mixing. The components may also be kept separate by being a simple non-miscible mixture of two phases.

The soap of this invention may be made to indicate that a presumably sufficient time has passed by any mechanism that may be observed by a user; color, smell, sound, temperature, and viscosity change and a combination thereof. These indicators may be activated through changes in pH, oxidation and reduction, metal complexing and gelation.

These indicators may also be used to ensure that all areas one desires to have cleaned, whether on the hands, another body part, or another surface, have indeed been cleaned.

Changes in color may be from colorless to colored, colored to colorless, or from one color to another. The viscosity change may be from liquid to gel, liquid to paste, liquid to solid, and any permutation thereof. A sound may be generated or terminated at the appropriate time or a smell may be generated, for example, for users unable to see color change.

The following embodiments illustrate the invention in varying scope.

An indicating soap was made starting with standard colorless, over-the-counter liquid soap, Kimberly-Clark Professional antibacterial Clear Skin Cleanser (PCSC C2001-1824). A small amount of food grade dye, in this case 0.2 weight percent of FD&C (food, drug & cosmetic) green dye number 3 from BF Goodrich of Cincinnati, Ohio, was added to the liquid soap. Mixed separately were antibacterial soap and a decolorizing agent. The decolorizing agent was 1 weight percent ascorbic acid from Aldrich Chemical Company of Milwaukee, Wis. and 1 weight percent iron chloride also from Aldrich Chem. Co. When the two components are mixed in approximately equal proportions in the hand, for example, the color will initially be green. After about 30 seconds the color will gradually change to blue. The speed of the color change is controlled by the concentration of the decolorizing agent. The residual blue color is useful in indicating how thoroughly the hands have been rinsed after use.

The viscosity changes of polymer solutions can be induced by many factors. One of them with viscosity increasing can be achieved by chemically or physically increasing the apparent molecular weight of polymers. The chemical methods include crosslinking reactions such as poly(vinyl alcohol) solution mixed with borax, while the physical methods include forming inter-polymer complexes such as hydrogen-bonding, hydrophobic, and polyelectrolyte complexes. On the other hand, solutions of some special chemicals are dilatant or rheopexy fluids. Their viscosity changes with shear rate or time, and hence can also be incorporated into liquid soaps to induce viscosity changes.

In a viscosity changing embodiment of the invention, the same colorless liquid soap (PCSC C2001-1824) was used. FD&C green dye number 3 in an amount of 0.2 weight percent and 5 weight percent of polyvinyl alcohol from Aldrich Chemical, having an average molecular weight of 85,000 to 146,000 and 87 to 89 percent hydrolyzed, was added to the soap to make a first component. In this case, a mixture of 0.2 weight percent sodium tetraborate decahydrate (Aldrich Chem.) and 2 weight percent citric acid in liquid soap was the second component When the two components were mixed, a gel was formed in the hand. After some time, dependent in this case upon the concentration of the citric acid, the gel is broken down and the soap has a water-like consistency.

In another viscosity changing embodiment of the invention, about same amount of an ion sensitive water-soluble polymer and liquid soap (PCSC C2001-1824) are applied from a two-chamber dispenser onto the hands. The system viscosity dramatically increased and became very sticky in the hand washing process. The mixture is also easy to rinse off the hand with water. The ion sensitive polymeric materials are described in U.S. Pat. No. 6,194,517 to Pomplun et al., commonly assigned, which issued Feb. 27, 2001 and in allowed U.S. patent application Ser. No. 09/223,999, filed Dec. 31, 1998. The patent teaches water soluble polymers comprising from about 25 to about 90 weight percent of an unsaturated carboxylic acid/unsaturated carboxylic acid ester co-polymer; from about 10 to about 75 weight percent of a divalent ion inhibitor and from about 0 to about 10 weight percent of a plasticizer. The polymers are soluble in an aqueous environment having a divalent ion concentration less than about 50 ppm and a monovalent ion concentration of less than about 0.5 weight percent. The polymers are insoluble in an aqueous solution having a concentration of divalent ions greater than about 50 ppm.

Poly(acrylic acid) (from Aldrich, MW 45,000) was incorporated into liquid soap (PCSC C2001-1824) with concentration of 10 weight percent. The mixture can be easily applied onto the hands similar to the original liquid soap, but is very sticky in the hand washing process, and generates sticky fibers between the hands whenever the hands are separated. The mixture is easy to rinse off the hands with water.

PLURONIC® F127 NF block copolymer and liquid soap (PCSC C2001-1824) solution was prepared with PLURONIC® F127 NF concentration of 15 weight percent. This solution and a 10 weight percent poly(acrylic acid) (from Aldrich, MW 45,000) were applied onto hands from a two-chamber dispenser. The mixture has an obvious viscosity increase and becomes very sticky in the hand washing process, yet is easy to rinse off the hands with water. Using 5 weight percent poly(vinyl alcohol) (from Aldrich, 99 percent hydrolyzed, MW 85,000–146,000) instead of 15 weight percent PLURONIC® F127 NF has the similar effect. It should be noted that the viscosity increases can also be induced by temperature-responsive polymers alone, i.e. by the use of PLURONIC® type block co-polymers without the use of polyacrylic acid.

Block copolymers suitable for use in this system include polyols and those of polyethylene glycol/poly(lactic-co-glyclic) acid. Commercially available block copolymers include PLURONIC® and TETRONIC® from BASF. Useful polyoxybutylene based block copolymers conform to the following generic formula:

$$HO(C_2H_4O)_b(C_4H_8O)_a(C_2H_4O)_bH$$

wherein a and b are integers such that the hydrophobe base represented by ($C_4H_8O$) has a molecular weight of at least about 500, preferably, at least about 1000 and most preferably, at least about 3000, as determined by hydroxyl number, the polyoxyethylene chain constituting at least about 60%, preferably, at least about 70% by weight of the copolymer and the copolymer having a total average molecular weight of at least about 5000, preferably, at least about 10,000, and most preferably, at least about 15,000.

The copolymer is characterized in that all the hydrophobic oxybutylene groups are present in chains bonded to an organic radical at the former site of a reactive hydrogen atom thereby constituting a polyoxybutylene base copolymer. The hydrophilic oxyethylene groups are used to cap the polyoxybutylene base polymer.

Polyoxyethylene-polyoxypropylene block copolymers which can be used to form aqueous gels can be represented by the following formula:

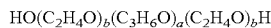

$$HO(C_2H_4O)_b(C_3H_6O)_a(C_2H_4O)_bH$$

wherein a and b are integers such that the hydrophobe base represented by ($C_3H_6O$) has a molecular weight of at least about 900, preferably, at least about 2500, most preferably, at least about 4000 average molecular weight, as determined by hydroxyl number; the polyoxyethylene chain constituting at least about 60%, preferably, at least about 70% by weight of the copolymer and the copolymer having a total average molecular weight of at least about 5000, preferably, at least about 10,000, and most preferably, at least about 15,000.

In addition to those polyoxyalkylene block copolymers referred to above, which are suitable in the formation of the compositions of the invention, other polyoxyalkylene polymers which form gels at low concentrations in water are suitable. One such polymer is described in U.S. Pat. No. 4,810,503, incorporated herein by reference. These polymers are prepared by capping conventional polyether polyols with an alpha-olefin epoxide having an average of about 20 to about 45 carbon atoms, or mixtures thereof. Aqueous solutions of these polymers gel in combination with surfactants, which can be ionic or nonionic. The combination of the capped polyether polymers and the surfactants provide aqueous gels at low concentrations of the capped polymer and surfactant, which generally do not exceed 10% by weight total. Detailed methods of preparing these aqueous gels are disclosed in U.S. Pat. No. 4,810,503.

A CELQUAT® H-100 (a cationic cellulose quarternary ammonium derivative from National Starch & Chemicals) and liquid soap (PCSC C2001-1824) solution was prepared with CELQUAT® H-100 concentration of 1.5 weight percent. This solution and a 10 weight percent poly(acrylic acid) (from Aldrich, MW 45,000) were applied onto the hands from a two-chamber dispenser. The mixture has an obvious viscosity increase and becomes very sticky in the hand washing process, yet is easy to rinse off the hands with water.

In still another embodiment, the methods above were combined to produce a soap that changed color and viscosity. The antibacterial liquid soap (PCSC C2001-1824) was again the base material. FD&C green dye number 3 in an amount of 0.1 weight percent and 5 weight percent polyvinyl alcohol were added to the soap to make one component. A second component was made with liquid soap, 0.2 weight percent FD&C yellow dye number 5 (BF Goodrich), 1 weight percent sodium tetraborate decahydrate. A third component was 2 weight percent citric acid dissolved in water. Upon mixing the components, a green gel is formed. After a time of about 30 seconds, the soap's viscosity was reduced and its color slowly changed to blue.

In still another embodiments, the antibacterial liquid soap (PCSC C2001–1824) was again the base material and the following general preparation was used for all the experiments:

20 ml of the liquid soap was made containing 0.01 weight percent dye. This was physically mixed to ensure uniformity of color throughout the liquid.

20 ml of liquid soap was prepared containing 0.05 weight percent citric acid (Aldrich Chemical Co, Milwaukee, Wis.) and mixed to ensure it was homogeneously dissolved.

20 ml of liquid soap was prepared containing 0.05 weight percent sodium carbonate (Aldrich Chemical Co., Milwaukee, Wis.) and mixed to ensure it was dissolved into the soap.

20 ml of liquid soap was prepared containing 0.01 weight percent copper chloride (Aldrich Chemical Co., Milwaukee, Wis.) was dissolved into the liquid soap.

Approximately 5 ml of the dye containing liquid soap was mixed with an equal volume of liquid soap containing the "activating agent" (e.g. citric acid etc) and the color change noted.

| | COLOR CHANGE | | |
|---|---|---|---|
| DYE | FROM | TO | AGENT |
| Red 28 | Colorless | Fluorescent red | Citric acid |
| Red 27 | Pink | Blue | Copper ion |
| Red 30 | Yellow | Red | Sodium Carbonate |
| FD & C Dyes (from BF Goodrich, Cincinnati, Ohio) | | | |
| Green 3 | Green | Blue | Sodium Carbonate |
| Yellow 6 | Red | Yellow | Citric acid |
| Food/Beverage Dyes (from Aldrich Chemical Co., Milwaukee, WI) | | | |
| New Coccine | Red | Violet | Sodium Carbonate |
| Litmas | Pink | Purple | Sodium Carbonate |
| Carminic acid | Pink | Purple | Sodium Carbonate |
| Other Dyes | | | |
| Alizarin complexone | Yellow | Purple | Sodium Carbonate |
| Neutral Red | Red | Yellow | Sodium Carbonate |
| Thymol blue | Yellow | Blue | Sodium Carbonate |
| Phenolphthalein | Colorless | Magenta | Sodium Carbonate |
| Chlorophenol red | Yellow | Red | Sodium Carbonate |

-continued

| DYE | COLOR CHANGE | | AGENT |
| --- | --- | --- | --- |
| | FROM | TO | |
| Bromothymol blue | Yellow | Green | Sodium Carbonate |
| Nitrazine yellow | Yellow | Purple | Sodium Carbonate |

Thus, a variety of color changing chemistries are available for the liquid soap formulations.

The soap of this invention may be dispensed by any convenient means known to be useful in dispensing two-component systems. Such dispensers are known in the art for dispensing shampoo and the like. These systems may use a squeeze bottle or a single plunger-type pump that displaces an approximately equal volume of each component simultaneously. A disposable form of this method of dispensing includes two components and a separator in a flexible pouch that may be torn or cut in a manner that allows both components to be released. Examples of such dispensers may be found in U.S. Pat. No. 5,645,822.

As will be appreciated by those skilled in the art, changes and variations to the invention are considered to be within the ability of those skilled in the art. Examples of such changes are contained in the patents identified above, each of which is incorporated herein by reference in its entirety to the extent it is consistent with this specification. Such changes and variations are intended by the inventors to be within the scope of the invention.

What is claimed is:

1. A cleaning aid comprising a composition of a first component comprising a soap and a dye and a second component comprising ascorbic acid and iron chloride with said first component and said second component being separated from each other, wherein, upon dispensing said composition, said first component and said second component mix and react to produce an observable indicator after a period of time after dispensing of said composition and mixing of said first component and said second component.

2. The soap of claim 1 wherein said indicator includes said soap changing in color.

3. The soap of claim 1 wherein said indicator includes said soap changing in viscosity.

4. The soap of claim 1 wherein said indicator includes said soap changing in smell.

5. The soap of claim 1 wherein said indicator includes said soap changing in sound.

6. The soap of claim 1 wherein said indicator includes said soap changing in temperature.

7. The soap of claim 1 wherein said indicator includes said soap changing in from a finite time to at most 5 minutes.

8. The soap of claim 6 wherein said indicator includes said soap changing in between 25 and 35 seconds.

9. A soap for cleaning comprising a first component including liquid soap, a dye and polyvinyl alcohol, and a second component including borax, citric acid, ascorbic acid and iron chloride, wherein said components are mixable together to produce said soap.

10. The soap of claim 9 wherein said soap changes viscosity from a gel to a liquid and simultaneously changes color from green to blue.

11. The soap of claim 1 wherein said indicator includes said soap changing viscosity and color in from a finite time to at most 45 seconds after said components are mixed together.

12. The soap of claim 3 wherein said indicator includes said soap changing viscosity and color between 25 and 35 seconds after said components are mixed together.

13. The soap of claim 1 wherein said indicator includes said soap changing in from 10 to 45 seconds.

14. The soap of claim 1 wherein said indicator includes said soap changing in from a finite time to at most 2 minutes.

* * * * *